United States Patent [19]

Schwarze et al.

[11] 4,358,459
[45] Nov. 9, 1982

[54] CYCLOPROPANE CARBOXYLIC ACID AND PROCESS FOR THEIR PRODUCTION AND USE

[75] Inventors: Werner Schwarze, Frankfurt; Axel Kleemann, Hanau, both of Fed. Rep. of Germany

[73] Assignee: Degussa Aktiengesellschaft, Frankfurt, Fed. Rep. of Germany

[21] Appl. No.: 217,443

[22] Filed: Dec. 17, 1980

[30] Foreign Application Priority Data

Dec. 22, 1979 [DE] Fed. Rep. of Germany ....... 2951939

[51] Int. Cl.³ .................... C07C 69/74; A01N 53/00
[52] U.S. Cl. ............................... 424/283; 549/427; 560/124; 424/305; 424/306
[58] Field of Search ............... 560/124; 424/305, 306, 424/283; 260/345.8 R

[56] References Cited

U.S. PATENT DOCUMENTS 3,856,976 12/1974 Hunter .................... 424/305
3,925,460 12/1975 Henrick .................. 560/124
3,957,849 5/1976 Henrick .................. 560/124

FOREIGN PATENT DOCUMENTS 53-90249 1/1977 Japan .

OTHER PUBLICATIONS

Sugawara, Agric. Biol. Chem., 42, pp. 847–850 (1978).

*Primary Examiner*—Michael L. Shippen
*Attorney, Agent, or Firm*—Cushman, Darby & Cushman

[57] ABSTRACT

There are prepared new cyclopropane carboxylic acid esters, particularly the tetrahydrobenzyl ester. They have insecticide and ovicide activity. The compounds are prepared by known methods of esterification.

33 Claims, No Drawings

CYCLOPROPANE CARBOXYLIC ACID AND PROCESS FOR THEIR PRODUCTION AND USE

SUMMARY OF THE INVENTION

The present invention is directed to cyclopropane carboxylic acid esters, processes for their production and their use as pesticides.

The cyclopropane carboxylic acid esters of the invention have the formula $$\begin{array}{c} R_2 \quad R_1 \quad O \\ | \quad | \quad \| \\ R_3-C \underset{\diagdown}{\overset{\diagup}{\rule{0pt}{8pt}}} C-C-O-CH_2-R_6 \\ \underset{R_4}{\diagup} C \underset{R_5}{\diagdown} \end{array} \quad (I)$$

wherein $R_1$, $R_2$, $R_3$, $R_4$ and $R_5$ are either hydrogen, halogen, alkyl or alkenyl, $R_6$ is the group $$\begin{array}{cc} \overset{CH_2}{\underset{R_7-CH}{\diagup}} \overset{}{\underset{\diagdown}{\rule{0pt}{8pt}}} CH, & \overset{CH_2}{\underset{R_7-CH}{\diagup}} \overset{}{\underset{\diagdown}{\rule{0pt}{8pt}}} CH-R_9 \quad \text{or} \\ -C-R_8 \quad \| \\ \diagdown X_1 \diagup & -C-R_8 \quad CH-R_{10} \\ & \diagdown X_1 \diagup \end{array}$$

$$\begin{array}{c} CH \\ CH_2 \quad | \quad CH \\ | \quad CH_2 \quad \| \\ R_8-C \quad \quad CH \\ \diagdown \quad | \quad \diagup \\ CH \end{array}$$

$R_7$ is a hydrogen atom, a methyl or phenyl group, $R_8$ is a hydrogen atom, a methyl group or the group $$\begin{array}{c} R_2 \quad R_1 \quad O \\ | \quad | \quad \| \\ R_3-C \underset{\diagdown}{\overset{\diagup}{\rule{0pt}{8pt}}} C-C-O-CH_2- \\ \underset{R_4}{\diagup} C \underset{R_5}{\diagdown} \end{array}$$

in which $R_1$ to $R_5$ are as defined above, $X_1$ is an oxygen atom, or the —$CH_2$— group and $R_9$ and $R_{10}$ are hydrogen atoms or halogen atoms. As halogen atoms there are included fluorine, chlorine, bromine or iodine, especially chlorine or bromine.

The alkyl and alkenyl groups of $R_1$ to $R_5$ can be straight or branched and preferably have 1 to 5 carbon atoms (2 to 5 carbon atoms for the alkenyl group). Examples of such alkyl groups are methyl, ethyl n-propyl, isopropyl, n-butyl, isobutyl, sec. butyl, tert.-butyl, n-pentyl and its isomers. Examples of alkenyl groups are 2-methyl propenyl, vinyl, allyl, propenyl, 2-methyl butenyl.

Because of their activity there are preferred compounds of formula I wherein $R_1$ is a hydrogen atom or a $C_1$-$C_5$ alkyl group, $R_2$, $R_3$, $R_4$ and $R_5$ each is a hydrogen atom or a methyl group, $R_6$ is the group $$\begin{array}{cc} \overset{CH_2}{\underset{R_7-CH}{\diagup}} \overset{}{\underset{\diagdown}{\rule{0pt}{8pt}}} CH \quad \text{or} & \overset{CH_2}{\underset{R_7-CH}{\diagup}} \overset{}{\underset{\diagdown}{\rule{0pt}{8pt}}} CH-R_9 \\ -C-R_8 \quad \| \\ \diagdown X_1 \diagup & -C-R_8 \quad CH-R_{10} \\ & \diagdown X_1 \diagup \end{array}$$

$R_7$ and $R_8$ each is a hydrogen atom, $X_1$ is an oxygen atom or the —$CH_2$— group and $R_9$ and $R_{10}$ each is a hydrogen, chlorine or bromine atom.

Especially preferred are compounds of formula I wherein $R_1$, $R_2$, $R_3$, $R_4$ and $R_5$ each is a hydrogen atom, $R_6$ is the group $$\begin{array}{cc} \overset{CH_2}{\underset{R_3-CH}{\diagup}} \overset{}{\underset{\diagdown}{\rule{0pt}{8pt}}} CH \quad \text{or} & \overset{CH_2}{\underset{R_7-CH}{\diagup}} \overset{}{\underset{\diagdown}{\rule{0pt}{8pt}}} CH-R_9 \\ -C-R_8 \quad \| \\ \diagdown X_1 \diagup & -C-R_8 \quad CH-R_{10} \\ & \diagdown X_1 \diagup \end{array}$$

$R_7$ and $R_8$ each is a hydrogen atom, $X_1$ is an oxygen atom or the —$CH_2$— group and $R_9$ and $R_{10}$ each is a hydrogen, chlorine or bromine atom.

Examples of compounds within formula I in addition to those in the working examples include
tetrahydrobenzyl 1,2,3-trimethylcyclopropane carboxylate,
tetrahydrobenzyl pentamethyl cyclopropane carboxylate,
tetrahydrobenzyl 1-ethyl cyclopropane carboxylate,
tetrahydrobenzyl 2-ethyl cyclopropane carboxylate,
tetrahydrobenzyl 2-propyl cyclopropane carboxylate,
tetrahydrobenzyl 1-isopropyl cyclopropane carboxylate,
tetrahydrobenzyl 2,2-diethyl cyclopropane carboxylate,
tetrahydrobenzyl-1-pentyl cyclopropane carboxylate,
tetrahydrobenzyl-2-pentyl cyclopropane carboxylate,
tetrahydrobenzyl-2,2-dimethyl-3-sec.butyl cyclopropane carboxylate,
tetrahydrobenzyl-2,2-dibromo-cyclopropane carboxylate,
2-methyltetrahydrobenzyl cyclopropane carboxylate,
1-methyltetrahydrobenzyl cyclopropane carboxylate,
1,2-dimethyltetrahydrobenzyl cyclopropane carboxylate,
2-phenyl tetrahydrobenzyl cyclopropane carboxylate,
2-methyldihydropyranylmethyl cyclopropane carboxylate,
3-methyldihydropyranylmethyl cycloproprane carboxylate,
dihydropyranylmethyl 2,2-dimethyl cyclopropane carboxylate,
dihydropyranylmethyl 2,2-dichlorocyclopropane carboxylate,
hexahydrobenzyl cyclopropane carboxylate,
hexahydrobenzyl 1-methyl cyclopropane carboxylate,
hexahydrobenzyl 2-methyl cyclopropane carboxylate,
hexahydrobenzyl 2,2-dimethyl cyclopropane carboxylate,
4-chloro-hexahydrobenzyl cyclopropane carboxylate,
2-methyl-hexahydrobenzyl cyclopropane carboxylate,
4,5-difluoro-hexahydrobenzyl cyclopropane carboxylate,
4,5-diiodo-hexahydrobenzyl cyclopropane carboxylate,
tetrahydropyranylmethyl cyclopropane carboxylate,
bicyclo-[2,2,1]-heptene-5-methyl cyclopropane carboxylate,
dihydropyran dimethanol bis (cyclopropane carboxylic acid ester),
tetrahydropyran dimethanol bis (cyclopropane carboxylic acid ester),
cyclohexane-1,1-dimethanol bis (cyclopropane carboxylic acid ester).

The compounds of formula I can be prepared by known methods, e.g. by esterification or transesterification. For example, they can be produced as follows:

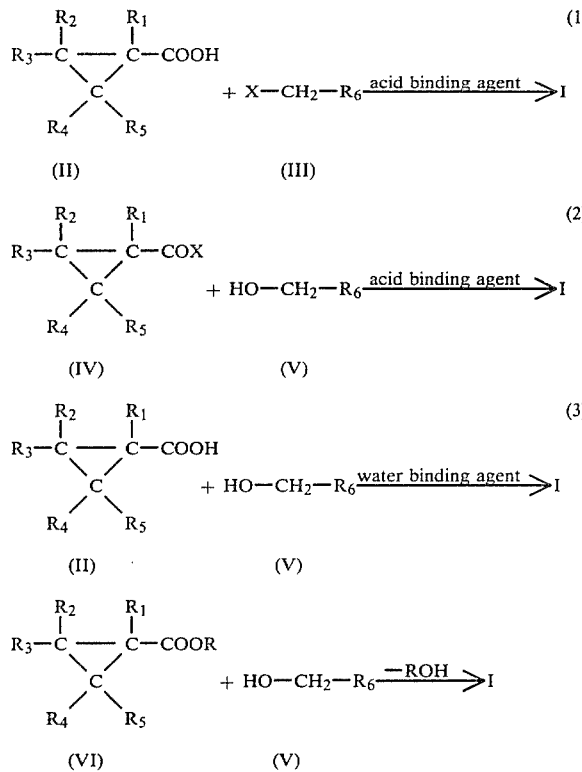

In formulae II to VI, $R_1$, $R_2$, $R_3$, $R_4$, $R_5$, and $R_6$ have the same meanings as those given in formula I.

In formula III and IV, X is a halogen atom, e.g. fluorine, chlorine, bromine, or iodine, especially chlorine or bromine and in formula VI, R is a $C_1$–$C_4$ alkyl group, e.g., methyl, ethyl, propyl, isopropyl, butyl, isobutyl, sec. butyl, especially methyl or ethyl. As acid binding agents for processes (1) and (2), there especially can be used tertiary amines such as trialkyl amines, e.g. trimethylamine, triethylamine, tributyl amine, diethyl propyl amine, and tris octyl amine, and pyridine, as well alkali metal and alkaline earth metal oxides, carbonates and bicarbonates such as sodium hydroxide, potassium hydroxide, calcium hydroxide, barium hydroxide, calcium oxide, barium oxide, sodium oxide, sodium carbonate, potassium carbonate, calcium carbonate, magnesium carbonate, sodium bicarbonate, potassium bicarbonate, calcium bicarbonate and magnesium bicarbonate, as well as alkali metal alcoholates, e.g. potassium t-butylate and sodium methylate. As water binding agents for process 3, there can be used for example bicyclohexylcarbodiimide. Processes (1) to (4) are carried out at a reaction temperature between $-10°$ and $+120°$ C., usually between 20° and 80° C., at normal or elevated pressure, and preferably in an inert solvent or diluent. As solvents or diluents, there are suited for example ethers and ether type compounds such as diethyl ether, dipropyl ether, dioxane, dimethoxyethane and tetrahydrofuran; amides such as N,N-dialkyl carboxylic acid amides, e.g. N,N-dimethyl formamide and N,N-dimethyl acetamide; aliphatic, aromatic and halogenated hydrocarbons, especially benzene, toluene, xylenes, chloroform and chlorobenzene, as well as hexane, decane, carbon tetrachloride, ethylene dichloride, decalin and tetralin; nitriles such as acetonitrile; dimethyl sulfoxide and ketones such as acetone and methyl ethyl ketone.

The esters of the saturated dibromo or dichloro hexahydrobenzyl alcohols also can be produced in other manners, for example by subsequently adding bromine or chlorine to the unsaturated tetrahydrobenzyl alcohol esters. This is equally valid for the unsaturated pyran alcohols.

The starting materials of formulae II to VI are known and can be produced according to known methods.

The compounds of formula I are suitable for controlling various kinds of animal and plant pests.

The compounds of formula I are especially suited for controlling insects, phytopathogenic mites and ticks, for example of the orders lepidoptera, coleoptera, homoptera, heteroptera, diptera, acarina, thysanoptera, orthoptera, anoplura, siphonaptera, mallophaga, thysanura, isoptera, psocoptera and hymenoptera.

Above all the compounds of formula I are suited for controlling eggs, larvae, nymphs, and imagines of plant injuring insects, especially plant injuring insect larvae in ornamental and useful plants, especially in cultivated cotton (for example against *Spodoptera littoralis* and *Heliothis virescens*) and cultivated vegetables (for example against *Leptinotarsa decemlineata* and *Myzus persicae*) and cultivated fruits (for example against *Laspeyresia pomonella*).

Active materials of formula I also show a very favorable activity against flies, as e.g. *Musca domestica* and mosquito larvae.

The acaricide or insecticide activity is substantially broadened by addition of other insecticides and/or acaricides and adjusted to the given circumstances. As additives, there are suited, e.g. organic phosphorus compounds, nitrophenols, and their derivatives; formamidines; ureas; other pyrethrine like compounds as well as carbamates and chlorinated hydrocarbons.

With especial advantage, the compounds of formula I are also combined with materials which exert a synergistic or reinforcing effect on pyrethroids. Examples of such compounds, among others, are piperonyl butoxide, propinyl ether, propinyl oxime, propinyl carbamate and propinyl phosphonate, 2-(3,4-methylenedioxyphenoxy)-3,6,9 trioxaundecane (Sesamex respectively Sesoxane), S,S,S-tributyl phosphorotrithioate, 1,2-methylendioxy-4-(2-(octylsulfinyl)-propyl)-benzene.

Compounds of formula I can be employed for their purposes alone or together with suitable carriers and/or additives. The suitable carriers and additives can be solid or liquid and correspond to the usual materials in the formulating art as, e.g. material or regenerated materials, solvents, dispersing agents, wetting agents, adhesive agents, thickening agents, binders, and/or fertilizers.

The production of the agents according to the invention takes place in a manner known of itself by intimately mixing and/or grinding the active materials of formula I with the suited carriers, in a given case with addition of dispersing agents or solvents inert to the active materials. The active materials can be present and are used in the following finished forms:

Solid finished forms: dusts, sprays, granulates (encased granulates, impregnated granulates, and homogeneous granulates);

Liquid finished forms:

(a) active concentrates dispersible in water: wettable powders, pastes, emulsions;
(b) solutions.

The content of active material in the above-described agents is between 0.1 and 95%, thereby it may be mentioned that in the application from airplanes or by means of other suitable application instruments, concentrations up to 99.5% or even pure material can be employed. The active materials of formula I for example can be formulated as follows (all parts are by weight):

Dusts:

For the production of a (a) 5% and (b) 2% dust, the following materials are used:

(a)

5 parts active material
95 parts talc (b)

2 parts active material
1 part highly dispersed silica
97 parts talc

The active material is mixed with the carriers and ground.

Granulates:

For the production of a 5% granulate, the following materials are used:
5 parts active material
0.25 part epoxidized vegetable oil
0.25 part cetyl polyglycol ether
3.50 parts polyethylene glycol
91 parts kaolin (particle size 0.3–0.8 mm).

The active material is mixed with the epoxidized vegetable oil and dissolved with 6 parts of acetone, upon this the polyethylene glycol and cetyl polyglycol ether added. The thus obtained solution is sprayed on kaolin and subsequently the acetone evaporated in a vacuum.

Wettable powder:

For the production of (a) 40%, (b) and (c) 25%, (d) 10% wettable powders, there are used the following components:

(a)

40 parts active material
5 parts sodium lignin sulfonate
1 part sodium dibutylnaphthalene sulfonate
54 parts silica (b)

25 parts active material
4.5 parts calcium ligninsulfonate
1.9 parts champagne chalk/hydroxyethyl cellulose mixture (1:1)
1.5 parts sodium dibutylnaphthalene sulfonate
19.5 parts silica
19.5 parts champagne chalk
28.1 parts kaolin (c)

25 parts active material
2.5 parts isooctylphenoxy polyethylene ethanol
1.7 parts champagne chalk/hydroxyethyl cellulose mixture (1:1)
8.3 parts sodium aluminum silicate
16.5 parts kieselguhr
46. parts kaolin (d)

10 parts active material
3 parts mixture of the sodium salts of saturated fatty alcohol sulfates
5 parts naphthalenesulfonic acid formaldehyde condensate
82 parts kaolin The active material is intimately mixed in suitable mixers with the additives and ground on corresponding mills and rolls. There are obtained wettable powders which can be diluted with water to form suspensions of any desired concentration.

Emulsifiable concentrates:

For the production of (a) 10%, (b) 25%, and (c) 50% emulsifiable concentrates, there were used the following materials:

(a)

10 parts active material
3.4 parts epoxidized vegetable oil
3.4 parts of a combination emulsifier consisting of fatty alcohol polyglycol ether and calcium alkylarylsulfonate
40 parts dimethyl formamide
43.2 parts xylene (b)

25 parts active material
2.5 parts epoxidized vegetable oil
10 parts of a mixture of alkylaryl sulfonate and fatty alcohol polyglycol ether
5 parts dimethyl formamide
57.5 parts xylene (c)

50 parts active material
4.2 parts tributylphenol-polyglycol ether
5.8 parts calcium dodecylbenzene sulfonate
20 parts cyclohexanone
20 parts xylene By dilution with water, there can be produced emulsions of any desired concentration from such concentrates.

Spraying agents:

For the production of a (a) and (b) 95% spraying agent, the following components are used:

(a)

5 parts active material
1 part epoxidized vegetable oil
94 parts gasoline (boiling range 160°–190° C.)

(b)

95 parts active material
5 parts epoxidized vegetable oil

Unless otherwise indicated, all parts and percentages are by weight.

The compositions can comprise, consist essentially of, or consist of the stated materials. They are applied in insecticidally or acaricidally effective amounts.

EXAMPLE 1

86 grams of cyclopropane carboxylic acid (1 mole) and 117.6 grams of tetrahydrobenzyl alcohol-1,2,3,6 (1.05 moles) were mixed with 400 ml of toluene, 2 grams of p-toluenesulfonic acid added and the mixture brought to boiling. The water formed in the esterification was removed azeotropically. After 2 hours, about 18 ml of water had been eliminated. The mixture was then cooled, washed with water (+ a little NaHCO$_3$) until neutral and the solution concentrated on a rotary evaporator. The residue was rectified on a 40 cm Vigreux column in a vacuum.

The tetrahydrobenzyl cyclopropane carboxylate distilled at B.P.$_{10}$ 122° C., amount: 148 grams, corresponding to 82.6% of theory.

Colorless liquid.

Analysis: C$_{11}$H$_{16}$O$_2$ (Mol. Wt. 180)—C, calculated, 73.3; found, 73.2. H, calculated, 8.88; found, 8.6.

EXAMPLE 2

180 grams of tetrahydrobenzyl alcohol (1,2,3,6) ester of cyclopropane carboxylic acid (1 mole) were dissolved in 1 liter of carbon tetrachloride. It was cooled to 0° C. Then there was run in a solution of 160 grams of bromine in 500 ml of carbon tetrachloride during which attention was paid that the reaction temperature did not exceed +5° C. The addition took place instantaneously. Subsequently, the mixture was washed neutral with water +NaHCO$_3$. The solution was concentrated on a rotary evaporator and subsequently distilled in a vacuum.

The cyclopropane carboxylic acid ester of 4,5-dibromo-hexahydrobenzyl alcohol-1 distilled at B.P.$_{2.5}$ 164°-166° C.

Colorless liquid, amount: 282.8 grams (83.2% of theory).

Analysis: C$_{11}$H$_{16}$Br$_2$O$_2$ (Mol. Wt. 340)— Calculated: C, 38.8, H, 4.7; Br, 47.1; found; C, 38.5; H, 4.7; Br, 48.1.

EXAMPLE 3

28.4 grams of 3-cyclohexene-1,1-dimethanol (0.2 mole) were dissolved in 150 ml of acetonitrile and 17.4 grams of pyridine (about 0.22 mole) added thereto. The mixture was cooled to 0° C. At this temperature, there were slowly dropped in 22 grams (about 0.21 mole) of cyclopropane carboxylic acid chloride, subsequently the mixture was slowly heated to room temperature (20° C.). After 2 hours the mixture was poured over ice. The oil which separated was shaken with methylene chloride. The organic phase was evaporated in a vacuum. There remained white crystals which were digested with petroleum ether and filtered off with suction. M.P. 76°-77° C., amount: 47.8 grams (86% of theory based on the formation of 3-cyclohexen-1,1-dimethanol bis (cyclopropane-carboxylic acid ester).

Analysis: C$_{16}$H$_{22}$O$_4$ (Mol. Wt. 278)—Calculated: C, 69.1; H, 7.9; Found: C, 69.3; H, 7.9.

EXAMPLE 4

128 grams of 2-methylcyclopropane carboxylic acid ethyl ester (1 mole) and 117.6 grams of tetrahydrobenzyl alcohol-1,2,3,6 (1.05 moles) were placed in 1 liter of toluene. Then there were added 2 grams of sodium ethylate and the mixture heated to boiling. The azeotrope toluene-ethanol was slowly distilled off over a 40 cm Vigreux column having a dephlegmator. The transesterification was finished in 6 hours.

The mixture was allowed to cool and then the reaction mixture was washed neutral, subsequently, the solvent was drawn off in a vacuum on the rotary evaporator. The residue was rectified in a vacuum. The 2-methyl-cyclopropane carboxylic acid ester of 1,2,3,6-tetrahydrobenzyl alcohol distilled at B.P.$_{15}$ 128°-130° C., 151 grams (77.9% of theory).

Analysis: C$_{12}$H$_{18}$O$_2$ (Mol. Wt. 194)—Calculated: C, 74.3; H, 9.3; Found: C, 74.1; H, 9.2.

EXAMPLE 5

46.2 grams of 2,2-dimethylol-bicyclo-[2,2,1]-heptene-5 (0.3 mole) and cyclopropane carboxylic acid (0.3 mole) were reacted with bicyclohexylcarbodiimide according to the method of A. Buzas et al., Compt. rend. 255, 945 (1962). There were obtained 30.4 grams of diester, B.P.$_{0.6}$ 152°-155° C. corresponding to a yield of 35.2% of theory.

Analysis: C$_{17}$H$_{22}$O$_4$ (Mol. Wt. 228)—Calculated: C, 71.0; H, 7.7; Found: C, 70.8; H, 7.8.

In analogous manner, there were produced the following compounds:

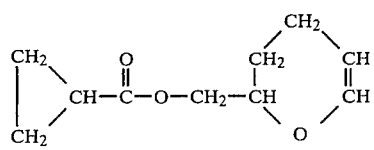

B.P.: 122° C./10 mm/Hg

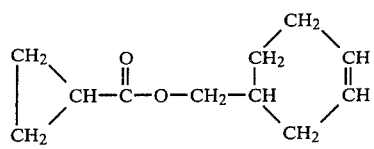

B.P.: 122° C./10 mm/Hg

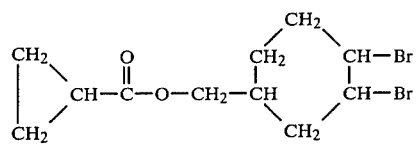

B.P.: 164–166° C./2.5 mm/Hg

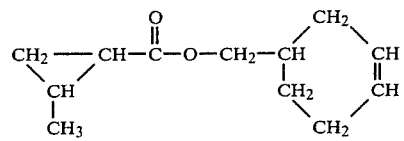

B.P.: 128–130° C./15 mm/Hg

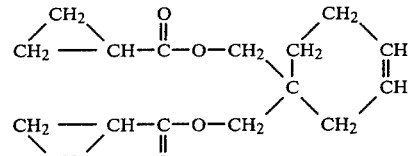

B.P.: 76–77° C.

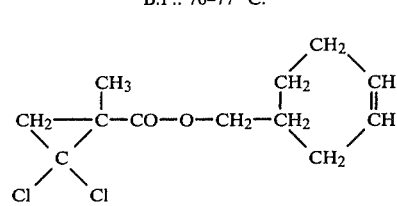

B.P.: 162–163° C./15 mm Hg

-continued

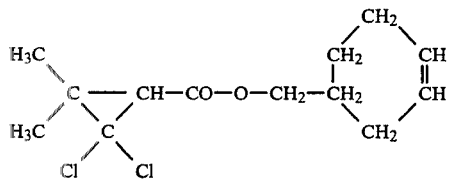

B.P.: 168–170° C./15 mm Hg

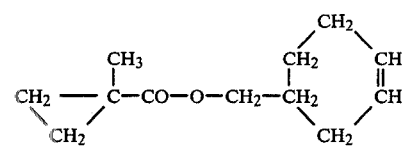

B.P.: 123–125° C./15 mm Hg

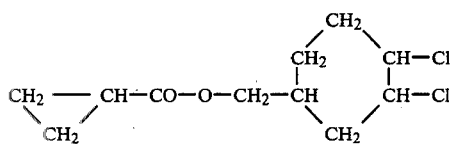

B.P.: 112–113° C./15 mm Hg

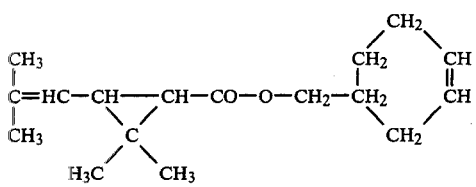

B.P.: 175–176° C./15 mm Hg

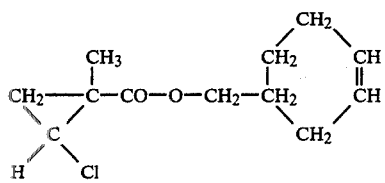

B.P.: 88° C./0.4 mm Hg

EXAMPLE 6

Insecticidal Stomach Poison Activity: *Spodoptera littoralis, Dysdercus fasciatus* and *Heliothis virescens*

Cotton plants were sprayed with an aqueous emulsion containing 0.05% of the compound being tested (obtained from a 10% emulsifiable concentrate).

After drying of the coating, the plants were each supplied with larvae of the species *Spodoptera littoralis* (L3-phase), *Dysdercus fasciatus* (L4) or *Heliothis virescens* (L3). There were used per test compound and per test species two plants and an evaluation of the killing rate produced took place after 2, 4, 24, and 48 hours. The tests were carried out at 24° C. and at 60% relative humidity.

The compounds of Example 5 in the above test showed a good activity against larvae of the species *Spodoptera litteroralis, Dysdercus fasciatus* and *Heliothis virescens.*

EXAMPLE 7

Insecticidal Stomach Poison Activity: *Leptinotarsa decemlineata*

With the same procedure using the larvae of the species *Leptinotarsa decemlineata* (L3) and potato plants in place of cotton plants, there was repeated the test method described in Example 6.

The compounds of Example 5 had a good activity against larvae of the species *Leptinotarsa decemlineata.*

EXAMPLE 8

Activity Against Plant Injuring Acarina: *Tetranychus Urticae* (OP-sensitive) and *Tetranychus Cinnabarinus* (OP-tolerant)

The primary leaves of Phaseolus vulgaris plants were coated 16 hours before the test for acaricide activity with a piece of leaf infested with a large quantity of *Tetranychus urticae* (OP-sensitive) or *Tetranychus cinnibarinas* (OP-tolerant). (The tolerance refers to the tolerance of Diazinon).

The thus treated infested plants were sprayed until dripping wet with a test solution containing 400 or 200 ppm of the compound being tested.

After 24 hours and again after 7 days, imagines and larvae (all motile phases) were evaluated under the binocular as to living and dead individuals.

There were used per concentration and per test species one plant. During the course of the test, the plants were kept in the greenhouse cabinet at 25° C.

The compounds according to Example 5 in this test showed a positive action against individuals of the species *Tetranychus urticae* and *Tetranychus cinnabarinus.*

EXAMPLE 9

Activity Against *Rhipicephalus bursu* (Imagines and Larvae), *Amblyomma hebraeum* (♀ Imagines, Nymphs and Larvae) and *Boophilus microplus* (Larvae-OP-sensitive and OP-tolerant)

As test objects there were used, larvae (in each case about 50), nymphs (each case about 25), or imagines (each case about 10) of *Rhipicephalus bursa, Amblyomma hebraeum* and *Boophilus microplus.* The test animals were dipped for a short time in an aqueous emulsion or solution containing 0.1; 1.0; 10; 50 or 100 ppm of the compound being tested. The emulsions or solutions situated in the test tubes were then absorbed on pads and the wetted test animals left in the thus contaminated tubes.

An evaluation of the killing rate obtained at each concentration took place for larvae after 3 days and for nymphs and imagines after 14 days.

The compounds according to Example 5 in this test showed a good activity against larvae, nymphs, and imagines of the species *Rhipicephalus bursa* and *Amblyomma hebraeum* as well as against larvae (OP-sensitive) of the species *Boophilus microplus.*

EXAMPLE 10

Activity Against *Musca domestica*

50 grams of freshly prepared CSMA nutritive substrate for maggots each time were weighed into beakers. A specific amount of a 1 weight % aqueous formulation of the active material in question (dispersible powder) was pipetted on the the nutritive substrate present in the beakers.

Then there were added per active material and concentration in each case 25 one day old maggots of *Musca domestica* in the breakers which contained the thus treated nutritive substrate. After the maggots had pupated the puppae formed were separated from the substrate by washing out with water and deposited in vessels closed with screen covers.

The puppae washed out per deposit were counted (toxic effect of the active material on the mite development). Then after 10 days the number of puppae which hatched into flies was determined.

The compounds of Example 5 showed a good activity against the hatching into flies in the above test.

EXAMPLE 11

Activity again *Aedes aegypti*

There was pipetted on the surface of 150 ml of water which was present in a beaker so much of a 0.1% emulsion preparation of the active material that concentrations of 10.5 and 1 ppm each were obtained. Then the containers were loaded with 30-40 2 day old Aëdes larvae. After 1, 2 and 5 days the mortality was examined.

The compounds of Example 5 in this test showed good activity against *Aedes aegypti*.

EXAMPLE 12

(a) Contact Activity on eggs of (a) *Spodoptera littoralis*

(b) *Heliothis virescens*

(c) *Laspeyresia pomonella*

The eggs were dipped for one minutes in a solution consisting of 8 ml of a 0.5% acetone solution of the compound being tested and 92 ml of water. After drying (about 1 hour) the eggs were placed in a petrie dish, stored for 4 days at 28° C. and then evaluated according to the percent hatched/not hatched. The compounds of Example 5 in this test showed a good activity against eggs of Spodotera littoralis, Heliothis virescens and Laspeyresia pomenella.

(b) Gas phase activity on eggs of *Spodoptera littoralis*

2 ml of 0.5% acetone solution of the test compound were pipetted into a petrie dish. An aluminum cylinder having a volume of 250 cc was placed in the treated petrie dish. The cylinder was divided half way up by a metal screen. Two eggs were placed on the metal screen per product. The cylinder was closed air-tight with cellophane paper. The test control was obtained after four days on percent hatching.

The compounds of Example 5 shows good gas phase activity against eggs of *Spodoptera littoralis*.

What is claimed is:

1. A cyclopropane carboxylic acid ester of the formula (I)

$$R_3-\underset{\underset{R_4}{\overset{\diagup}{\underset{C}{\diagdown}}R_5}}{\overset{R_2}{\underset{|}{C}}}-\overset{R_1}{\underset{|}{C}}-\overset{O}{\underset{||}{C}}-O-CH_2-R_6 \qquad (I)$$

wherein $R_1$, $R_2$, $R_3$, $R_4$, and $R_5$ are either hydrogen, halogen, or alkyl, $R_6$ is the group $$R_7-\overset{|}{\underset{|}{CH}}\overset{\diagup CH_2 \diagdown}{\underset{\diagdown X_1 \diagup}{}}\overset{}{\underset{}{CH}} ,\quad R_7-\overset{|}{\underset{|}{CH}}\overset{\diagup CH_2 \diagdown}{\underset{\diagdown X_1 \diagup}{}}\overset{}{\underset{}{CH-R_9}} \text{ or}$$

(with $-C-R_8$ below $R_7-CH$, and $CH$ or $CH-R_{10}$)

$$R_8-C \text{ (cyclohexene ring with } CH_2, CH_2, CH_2, CH, CH)$$

$R_7$ is a hydrogen atom, a methyl or phenyl group, $R_8$ is a hydrogen, a methyl group or the group $$R_3-\underset{\underset{R_4}{\overset{\diagup}{\underset{C}{\diagdown}}R_5}}{\overset{R_2}{\underset{|}{C}}}-\overset{R_1}{\underset{|}{C}}-\overset{O}{\underset{||}{C}}-O-CH_2-$$

$X_1$ is an oxygen atom or the $-CH_2-$ group and $R_9$ and $R_{10}$ are hydrogen or halogen when $X_1$ is an oxygen atom and $R_9$ and $R_{10}$ are halogen when $X_1$ is the $-CH_2-$ group, with the proviso that when $R_6$ is the group $$R_7-\overset{|}{\underset{|}{CH}}\overset{\diagup CH_2 \diagdown}{\underset{\diagdown X_1 \diagup}{}}\overset{}{\underset{||}{CH}}$$

and $X_1$ is the $-CH_2-$ group, not more than one of $R_4$ and $R_5$ can be alkyl and that not more than one of $R_2$ and $R_3$ can be alkyl unless at least one of $R_4$ and $R_5$ is halogen.

2. A compound according to claim 1 wherein $R_1$, $R_2$, $R_3$, $R_4$ and $R_5$ are hydrogen or alkyl of 1 to 5 carbon atoms.

3. A compound according to claim 1 wherein 0 to 3 of $R_1$, $R_2$, $R_3$, $R_4$ and $R_5$ are alkyl of 1 to 5 carbon atoms, 0 to 2 of $R_4$ and $R_5$ are chlorine or bromine, the balance of $R_1$, $R_2$, $R_3$, $R_4$ and $R_5$ are hydrogen with the proviso that not over 3 of $R_1$, $R_2$, $R_3$, $R_4$ and $R_5$ are alkyl, chlorine or bromine.

4. A compound according to claim 3 wherein 1 to 2 of $R_4$ and $R_5$ are chlorine or bromine and the balance of $R_1$, $R_2$, $R_3$, $R_4$ and $R_5$ are hydrogen or alkyl of 1 to 5 carbon atoms.

5. A compound according to claim 3 wherein 0 to 3 of $R_1$, $R_2$, $R_3$, $R_4$ and $R_5$ are alkyl of 1 to 5 carbon atoms and the balance of $R_1$, $R_2$, $R_3$, $R_4$ and $R_5$ are hydrogen.

6. A compound according to claim 1 wherein $R_1$ is hydrogen or a $C_1$-$C_5$ alkyl group, $R_2$, $R_3$, $R_4$, and $R_5$ are hydrogen or a methyl group, $R_6$ is the group $$R_7-\overset{|}{\underset{|}{CH}}\overset{\diagup CH_2 \diagdown}{\underset{\diagdown X_1 \diagup}{}}\overset{}{\underset{}{CH}} \text{ or } R_7-\overset{|}{\underset{|}{CH}}\overset{\diagup CH_2 \diagdown}{\underset{\diagdown X_1 \diagup}{}}\overset{}{\underset{}{CH-R_9}}$$

(with $-C-R_8$ and $-CH-R_8$ $CH-R_{10}$)

$R_7$ and $R_8$ are hydrogen, $X_1$ is oxygen or a $CH_2$ group and $R_9$ and $R_{10}$ are hydrogen, chlorine or bromine when $X_1$ is an oxygen atom and $R_9$ and $R_{10}$ are chlorine or bromine when $X_1$ is a $CH_2$ group.

7. A compound according to claim 1 wherein $R_1$, $R_2$, $R_3$, $R_4$ and $R_5$ are hydrogen, $R_6$ is the group

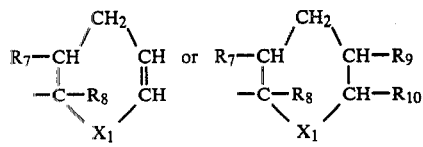

$R_7$ and $R_8$ hydrogen, $X_1$ is oxygen or a $CH_2$ group and $R_9$ and $R_{10}$ are hydrogen, chlorine or bromine when $X_1$ is an oxygen atom and $R_9$ and $R_{10}$ are chlorine or bromine when $X_1$ is a $CH_2$ group.

8. A compound according to claim 1 of the formula

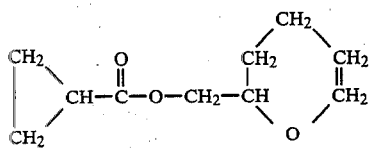

9. A compound according to claim 1 of the formula

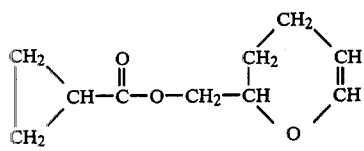

10. A compound according to claim 1 of the formula

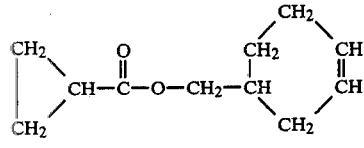

11. A compound according to claim 1 of the formula

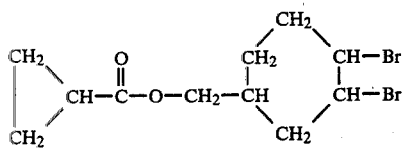

12. A compound according to claim 1 of the formula

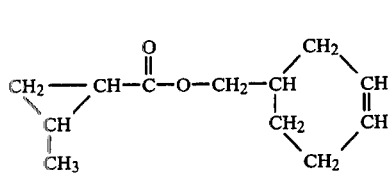

13. A compound according to claim 1 of the formula

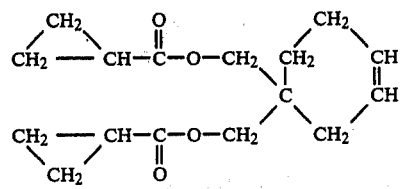

14. A compound according to claim 1 of the formula

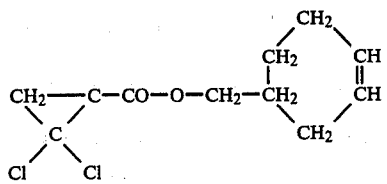

15. A compound according to claim 1 of the formula

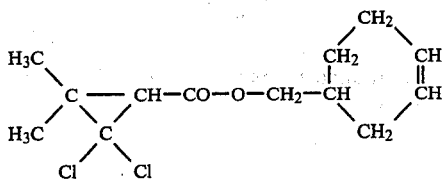

16. A compound according to claim 1 of the formula

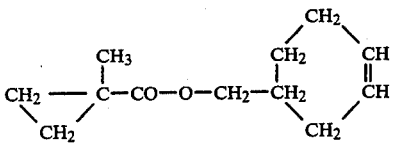

17. A compound according to claim 1 of the formula

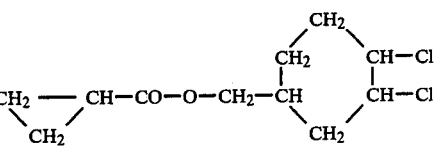

18. A compound according to claim 1 of the formula

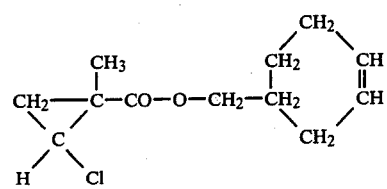

19. A compound according to claim 1 having the formula

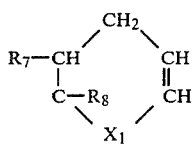

20. A compound according to claim 19 where $X_1$ is an oxygen atom.

21. A compound according to claim 19 where $X_1$ is the —$CH_2$— group.

22. A compound according to claim 21 where $R_2$ is hydrogen or halogen and $R_4$ is hydrogen or alkyl.

23. A compound according to claim 22 where $R_5$ is hydrogen.

24. A compound according to claim 23 where $R_4$ is hydrogen.

25. A compound according to claim 1 having the formula

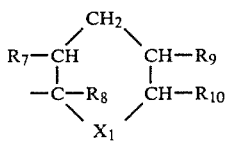

26. A compound according to claim 25 where $X_1$ is an oxygen atom.

27. A compound according to claim 25 where $X_1$ is the —$CH_2$— group.

28. A compound according to claim 1 having the formula

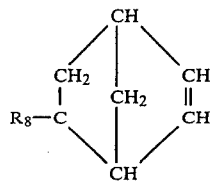

29. A pesticidal composition comprising as the active component aninsecticidally or acarinacidally effective amount of a compound according to claim 1 together with a carrier.

30. A method of controlling pests which are insects or members of the order acarina comprising applying to the insects or members of the acarina an insecticidally or acarinacidally effect amount of a compound of claim 1.

31. A method according to claim 30 wherein the pests are insects.

32. A method according to claim 30 wherein the pests are members of the order acarina.

33. A method according to claim 30 wherein the pests are in the form of eggs, larvae, nymphs or imagines.

* * * * *